United States Patent
Scheib et al.

(10) Patent No.: US 12,070,219 B2
(45) Date of Patent: Aug. 27, 2024

(54) PIVOTING ANVIL FOR SURGICAL CIRCULAR STAPLER

(71) Applicant: Cilag GmbH International, Zug (CH)

(72) Inventors: Charles J. Scheib, Loveland, OH (US); Steven G. Hall, Cincinnati, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/322,847

(22) Filed: May 24, 2023

(65) Prior Publication Data
US 2023/0293180 A1  Sep. 21, 2023

Related U.S. Application Data

(63) Continuation of application No. 17/090,378, filed on Nov. 5, 2020, now Pat. No. 11,690,625, which is a
(Continued)

(51) Int. Cl.
*A61B 17/072* (2006.01)
*A61B 17/115* (2006.01)
(Continued)

(52) U.S. Cl.
CPC . *A61B 17/1155* (2013.01); *A61B 2017/00477* (2013.01); *A61B 2017/07257* (2013.01);
(Continued)

(58) Field of Classification Search
CPC ............. A61B 17/1114; A61B 17/1155; A61B 2017/00477; A61B 2017/07257; A61B 2090/0811
(Continued)

(56) References Cited

U.S. PATENT DOCUMENTS 4,304,236 A  12/1981  Conta et al.
4,310,115 A   1/1982  Inoue
(Continued)

FOREIGN PATENT DOCUMENTS

DE  202010013152 U1  3/2011
EP      0698376 A2  2/1996
(Continued)

OTHER PUBLICATIONS

Meriam-Webster entry for term "freely", retrieved on Oct. 22, 2019, from https://www.merriam-webster.com/dictionary/freely.
(Continued)

*Primary Examiner* — Valentin Neacsu
(74) *Attorney, Agent, or Firm* — Frost Brown Todd LLP

(57) ABSTRACT

A circular stapler apparatus for stapling tissue has a circular stapling head operable to drive staples toward an anvil to form the staples in a circular array. The anvil includes an anvil head, a proximal shaft extending proximally from the anvil head and having a proximal end disposed in a first plane, and a first pivot connecting the anvil head to the proximal shaft. The first pivot is operable to be disposed in a second plane that is laterally offset from the first plane. The anvil is configured to rotate via movement through multiple pivot points. The anvil may be configured to rotate to a position in which a portion of the anvil head is disposed below the first pivot and between the first pivot and the proximal shaft such that the anvil head is acutely angled with respect to a longitudinal axis of the proximal shaft.

20 Claims, 10 Drawing Sheets

Related U.S. Application Data continuation of application No. 15/338,594, filed on Oct. 31, 2016, now Pat. No. 10,856,875, which is a continuation of application No. 13/688,992, filed on Nov. 29, 2012, now Pat. No. 9,498,222.

(51) Int. Cl.
*A61B 17/00* (2006.01)
*A61B 17/11* (2006.01)
*A61B 90/00* (2016.01)

(52) U.S. Cl.
CPC .... *A61B 17/1114* (2013.01); *A61B 2090/0811* (2016.02); *F04C 2270/041* (2013.01)

(58) Field of Classification Search
USPC ......... 227/175.1, 175.2, 176.1, 178.1, 179.1, 227/180.1; 606/33, 153, 219, 139
See application file for complete search history.

(56) References Cited

U.S. PATENT DOCUMENTS

| | | | |
|---|---|---|---|
| 4,505,414 A | 3/1985 | Filipi | |
| 4,700,703 A | 10/1987 | Resnick et al. | |
| 4,752,024 A | 6/1988 | Green et al. | |
| 4,805,823 A | 2/1989 | Rothfuss | |
| 4,893,622 A | 1/1990 | Green et al. | |
| 4,903,697 A | 2/1990 | Resnick et al. | |
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,411,508 A | 5/1995 | Bessler et al. | |
| 5,415,334 A | 5/1995 | Main et al. | |
| 5,465,895 A | 11/1995 | Williamson, IV et al. | |
| 5,533,661 A | 7/1996 | Knodel et al. | |
| 5,588,579 A | 12/1996 | Schnut et al. | |
| 5,597,107 A | 1/1997 | Knodel et al. | |
| 5,632,432 A | 5/1997 | Schulze et al. | |
| 5,639,008 A | 6/1997 | Gallagher et al. | |
| 5,673,840 A | 10/1997 | Schulze et al. | |
| 5,704,534 A | 1/1998 | Huitema et al. | |
| 5,704,898 A | 1/1998 | Kokish | |
| 5,732,872 A | 3/1998 | Bolduc et al. | |
| 5,758,814 A | 6/1998 | Gallagher et al. | |
| 5,814,055 A | 9/1998 | Knodel et al. | |
| 5,839,639 A | 11/1998 | Sauer et al. | |
| 5,860,581 A | 1/1999 | Robertson et al. | |
| 5,947,363 A | 9/1999 | Bolduc et al. | |
| 5,951,576 A | 9/1999 | Wakabayashi | |
| 6,053,390 A * | 4/2000 | Green .................. | A61B 17/115 227/19 |
| 6,485,496 B1 | 11/2002 | Suyker et al. | |
| 6,769,590 B2 | 8/2004 | Vresh et al. | |
| 6,783,524 B2 | 8/2004 | Anderson et al. | |
| 6,957,758 B2 * | 10/2005 | Aranyi ................. | A61B 17/115 227/176.1 |
| 6,978,921 B2 | 12/2005 | Shelton, IV et al. | |
| 7,000,818 B2 | 2/2006 | Shelton, IV et al. | |
| 7,018,387 B2 | 3/2006 | Suyker et al. | |
| 7,022,127 B2 | 4/2006 | Suyker et al. | |
| 7,080,769 B2 | 7/2006 | Vresh et al. | |
| 7,143,923 B2 | 12/2006 | Shelton, IV et al. | |
| 7,168,604 B2 | 1/2007 | Milliman et al. | |
| 7,303,108 B2 | 12/2007 | Shelton, IV et al. | |
| 7,325,713 B2 | 2/2008 | Aranyi | |
| 7,364,060 B2 | 4/2008 | Milliman | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,431,191 B2 | 10/2008 | Milliman | |
| 7,434,715 B2 | 10/2008 | Shelton, IV et al. | |
| 7,494,038 B2 | 2/2009 | Milliman | |
| 7,516,877 B2 | 4/2009 | Aranyi | |
| 7,546,940 B2 | 6/2009 | Milliman et al. | |
| 7,556,186 B2 | 7/2009 | Milliman | |
| 7,721,930 B2 | 5/2010 | McKenna et al. | |
| 7,784,662 B2 | 8/2010 | Wales et al. | |
| 7,802,712 B2 | 9/2010 | Milliman et al. | |
| 7,857,187 B2 | 12/2010 | Milliman | |
| 7,874,981 B2 | 1/2011 | Whitman et al. | |
| 8,109,426 B2 | 2/2012 | Milliman et al. | |
| 8,123,103 B2 | 2/2012 | Milliman | |
| 8,141,763 B2 | 3/2012 | Milliman | |
| 8,328,062 B2 | 12/2012 | Viola | |
| 8,328,063 B2 | 12/2012 | Milliman et al. | |
| 8,413,870 B2 | 4/2013 | Pastorelli et al. | |
| 8,496,157 B2 | 7/2013 | Olson | |
| 8,540,132 B2 | 9/2013 | Marczyk et al. | |
| 8,858,590 B2 | 10/2014 | Shelton, IV et al. | |
| 9,113,883 B2 * | 8/2015 | Aronhalt ............ | A61B 17/0293 |
| 9,492,172 B2 | 11/2016 | Weisshaupt et al. | |
| 9,498,222 B2 * | 11/2016 | Scheib ............... | A61B 17/1155 |
| 9,592,055 B2 | 3/2017 | Milliman et al. | |
| 10,856,875 B2 * | 12/2020 | Scheib ............... | A61B 17/1155 |
| 11,690,625 B2 | 7/2023 | Scheib et al. | |
| 2005/0205639 A1 * | 9/2005 | Milliman ............ | A61B 17/115 227/19 |
| 2006/0201989 A1 | 9/2006 | Ojeda | |
| 2007/0194081 A1 | 8/2007 | Hueil et al. | |
| 2008/0054045 A1 * | 3/2008 | Milliman .............. | A61B 17/068 227/175.1 |
| 2009/0082785 A1 * | 3/2009 | Milliman ............ | A61B 17/1155 606/139 |
| 2010/0038401 A1 * | 2/2010 | Milliman ............ | A61B 17/068 227/175.1 |
| 2011/0011916 A1 | 1/2011 | Levine | |
| 2011/0101065 A1 * | 5/2011 | Milliman ............ | A61B 17/068 227/175.1 |
| 2011/0152861 A1 * | 6/2011 | Weisshaupt .......... | A61B 17/115 606/41 |
| 2011/0295269 A1 | 12/2011 | Swensgard et al. | |
| 2012/0211544 A1 * | 8/2012 | Olson ............... | A61B 17/07207 227/176.1 |
| 2012/0239082 A1 * | 9/2012 | Shelton, IV ....... | A61B 17/0218 606/205 |
| 2012/0253367 A1 * | 10/2012 | Yamakawa ............ | A61B 17/11 606/153 |
| 2014/0144969 A1 * | 5/2014 | Scheib ............... | A61B 17/1155 227/175.1 |
| 2017/0042544 A1 * | 2/2017 | Scheib ............... | A61B 17/1155 |
| 2021/0169488 A1 * | 6/2021 | Scheib ............... | A61B 17/1155 |
| 2023/0293180 A1 * | 9/2023 | Scheib ............... | A61B 17/1155 227/175.1 |

FOREIGN PATENT DOCUMENTS

| | | |
|---|---|---|
| EP | 2153781 A2 | 2/2010 |
| EP | 2489311 A2 | 8/2012 |
| EP | 2505148 A1 | 10/2012 |
| JP | 2006-501950 A | 1/2006 |
| JP | 2007-307364 A | 11/2007 |
| JP | 2012-205718 A | 10/2012 |
| SU | 1242140 A1 | 7/1986 |
| WO | WO 2003/030745 A1 | 4/2003 |
| WO | WO 2004/112583 A2 | 12/2004 |
| WO | WO 2011/109988 | 9/2011 |

OTHER PUBLICATIONS

Chinese Office Action and Search Report dated Jan. 3, 2017, for Application No. 201380062163.6, 15 pages.
European Examination Report dated Sep. 12, 2016, for Application No. 13808330.8, 4 pages.
European Decision to Grant dated Jun. 7, 2018, for Application No. 13808330.8, 2 pages.

(56) References Cited

OTHER PUBLICATIONS

European Search Report and Written Opinion dated Oct. 17, 2018, for Application No. 18181393.2, 7 pages.
International Search Report dated Jun. 20, 2014, for International Application No. PCT/US2013/071622, 8 pages.
International Preliminary Report on Patentability and Written Opinion dated Jun. 2, 2015, for International Application No. PCT/US2013/071622, 11 pages.
Japanese Notification of Reasons for Refusal dated Jul. 4, 2017, for Application No. 2015-545140, 6 pages.
Japanese Notification of Reasons for Refusal dated Mar. 13, 2018 for Application No. 2015-545140, 5 pages.
Japanese Notification of Reasons for Refusal dated Sep. 25, 2018, for Application No. 2015-545140, 2 pages.
Russian Office Action and Search Report dated Oct. 26, 2017, for Application No. 2015125314, 7 pages.

* cited by examiner

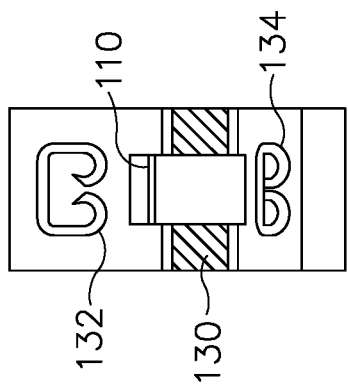
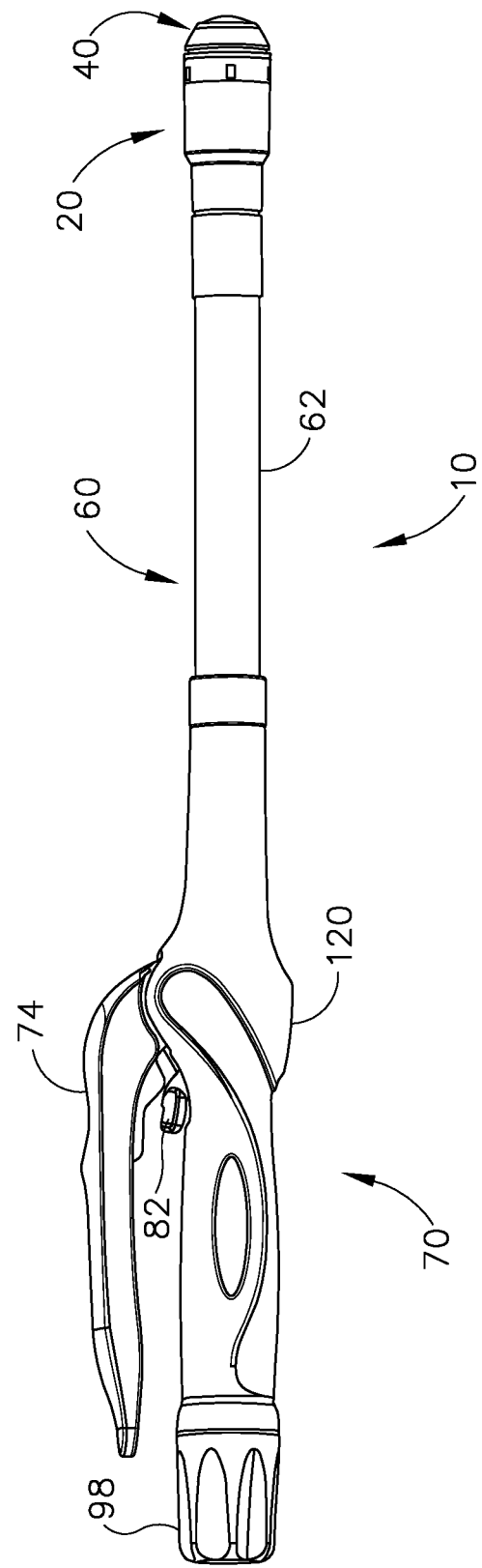
Fig.6
Fig.1

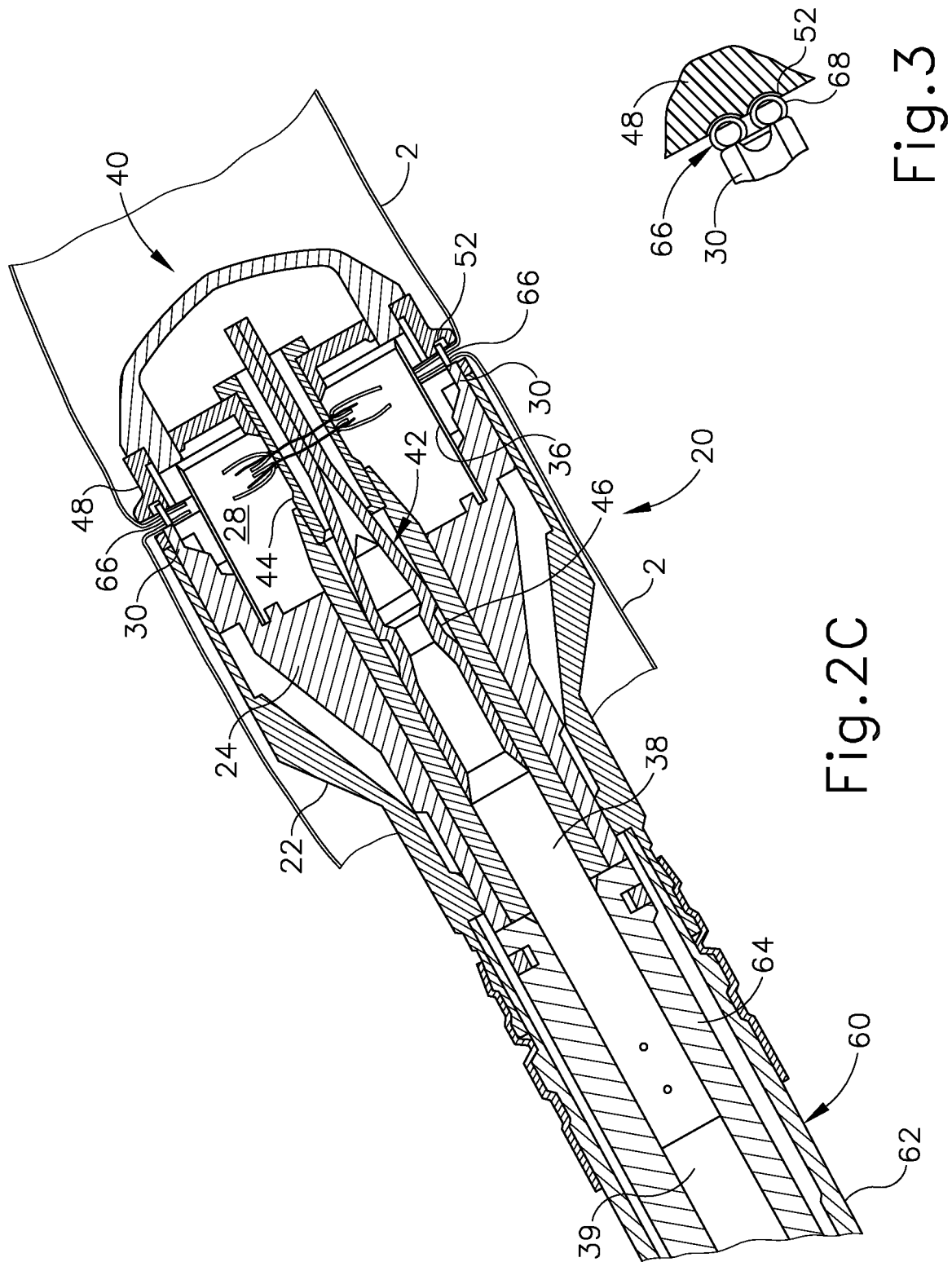

PIVOTING ANVIL FOR SURGICAL CIRCULAR STAPLER

This application is a continuation of U.S. patent application Ser. No. 17/090,378, filed Nov. 5, 2020, issued as U.S. Pat. No. 11,690,625 on Jul. 4, 2023, which is a continuation of U.S. patent application Ser. No. 15/338,594, filed Oct. 31, 2016, issued as U.S. Pat. No. 10,856,875 on Dec. 8, 2020, which is a continuation of U.S. patent application Ser. No. 13/688,992, filed on Nov. 29, 2012, issued as U.S. Pat. No. 9,498,222 on Nov. 22, 2016.

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. Patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side elevation view of an exemplary circular stapling surgical instrument;

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 6 depicts an diagrammatic view of the indicator window of FIG. 5 showing an exemplary indicator bar and exemplary corresponding staple representations;

Figure 2A:
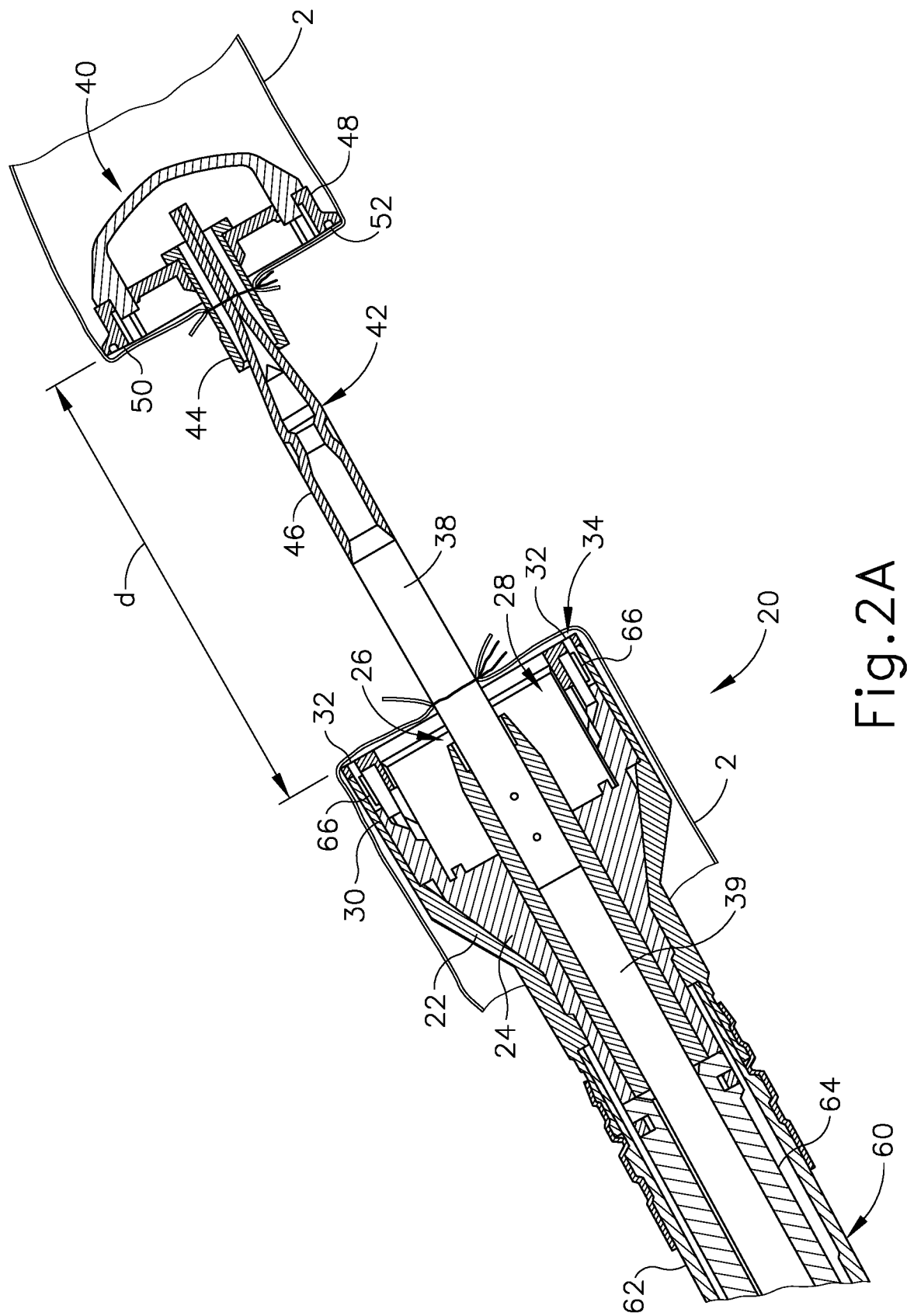
FIG. 2A depicts an enlarged longitudinal cross-section view of an exemplary stapling head assembly of the instrument of FIG. 1 showing an exemplary anvil in an open position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and an adjusting knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 2B:
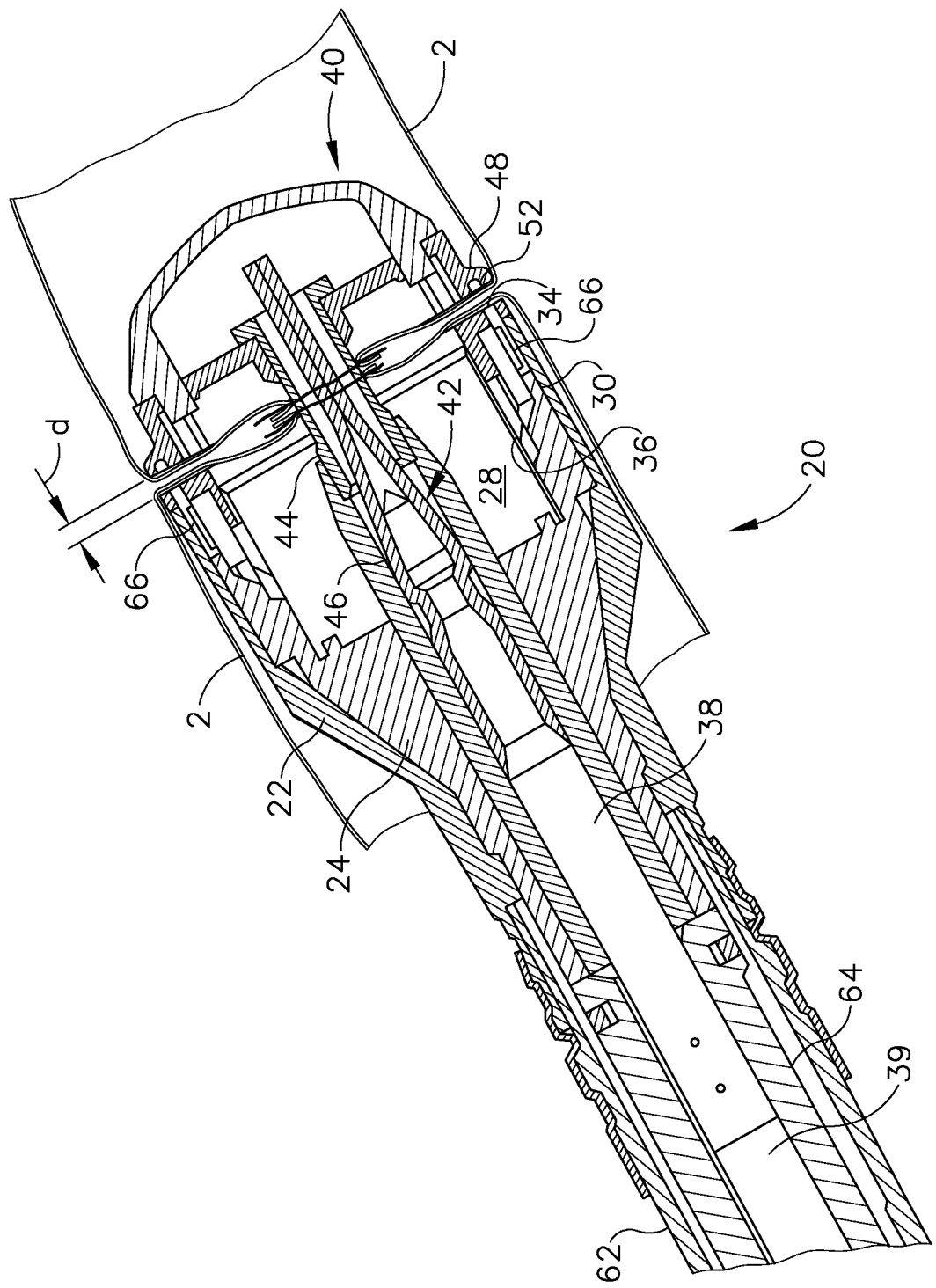
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples. It should be understood that staple forming pockets (52) are merely optional and may be omitted in some versions.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
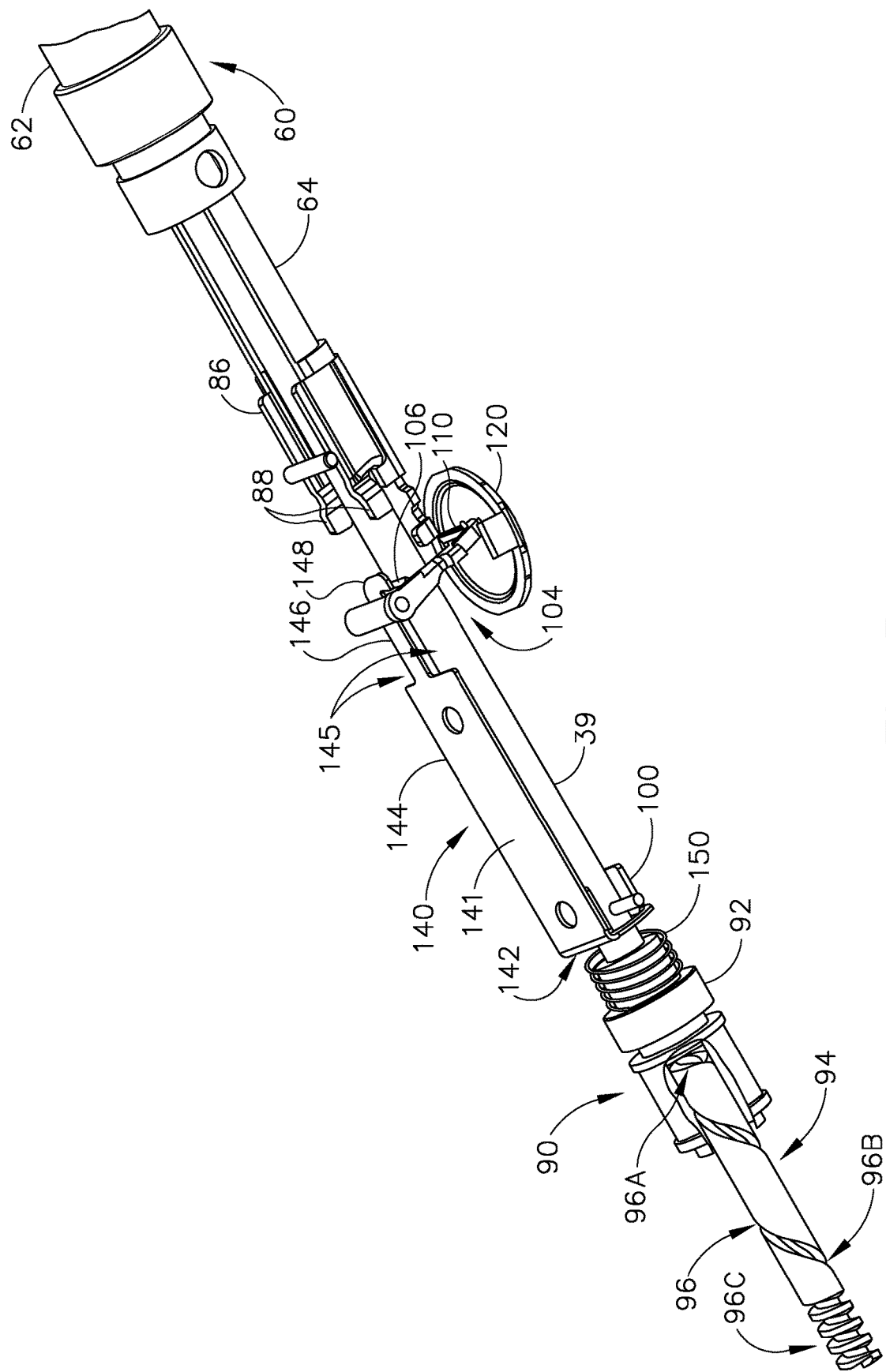
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of adjusting knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
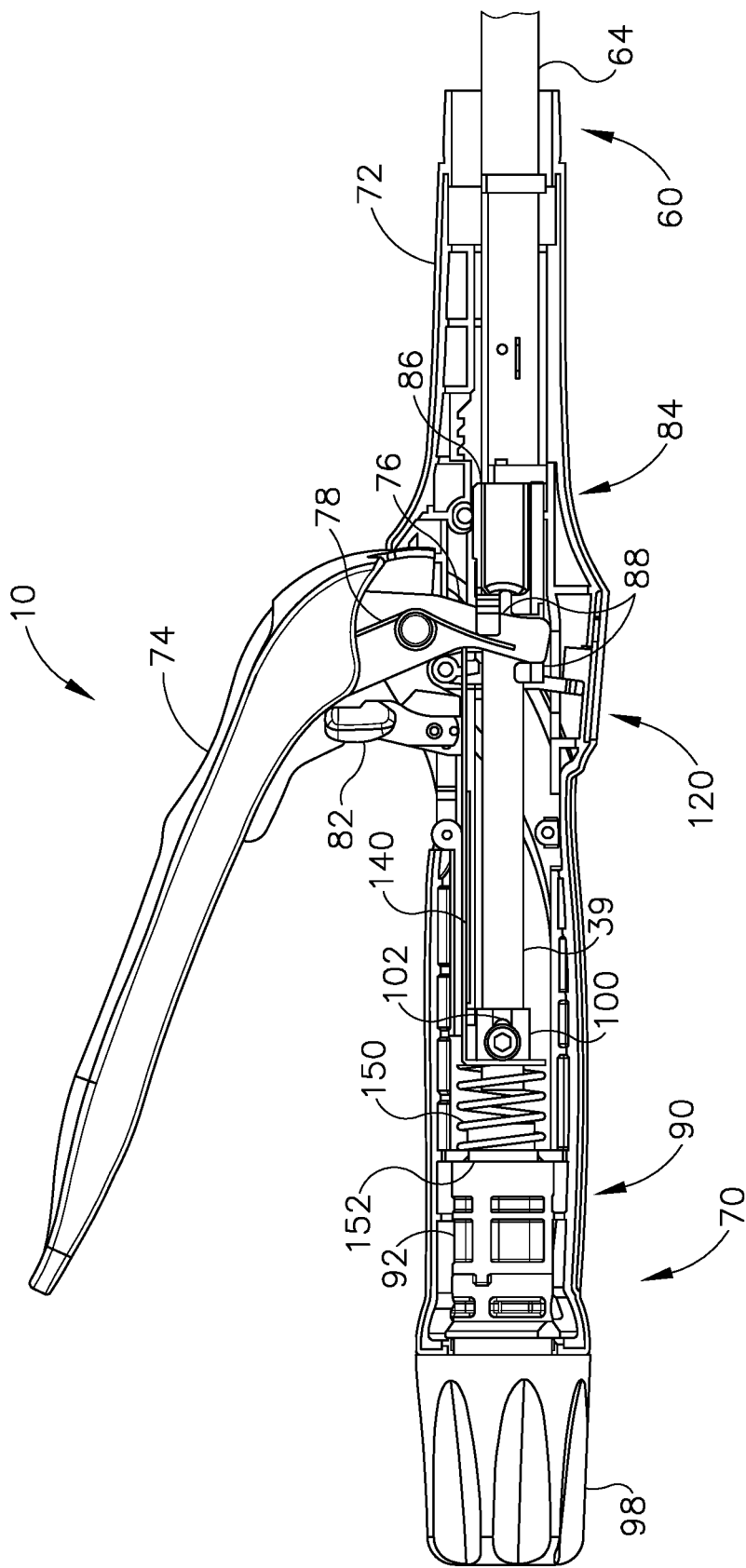
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
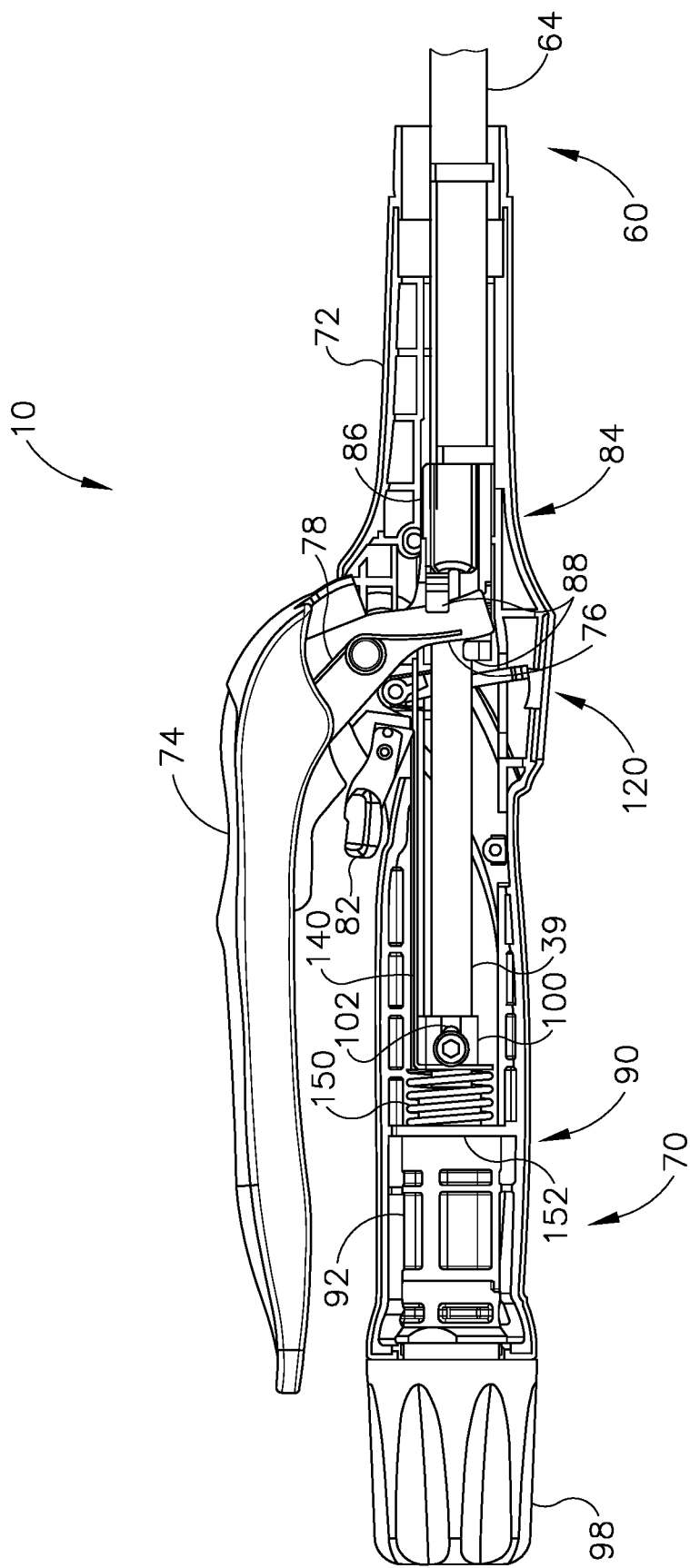
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). U-shaped clip (100) engages with a portion of body (72) to substantially prevent trocar actuator (39) from rotating about its axis when adjusting knob (98) is rotated. U-shaped clip (100) further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

II. Exemplary Anvil Tilting Versions

As described above, an anvil such as anvil (40) of FIG. 2A may be inserted into a lumen forming portion of tissue (2), and may be retracted from an anastomosis site being used as described above to staple portions of tissue (2) to form the anastomosis. For example, FIGS. 7A-9 show upper esophagus (4A) and lower esophagus (4B), which are formed by tissue (2) this is stapled together at an anastomosis (6). In an esophagectomy, for example, a surgeon may desire to introduce an anvil of a circular stapler trans-orally and in an atraumatic manner. For example, the surgeon may desire to reduce trauma that may occur to an interior surface of the esophagus via trans-oral introduction of the anvil, as well retraction of the anvil, by preventing an outer edge of the anvil from interacting with the interior surface of esophagus (4) during insertion and retraction of the anvil. Or the surgeon may wish to introduce the circular stapler anvil in an atraumatic manner in an intestinal procedure or like procedures as will be apparent to those of ordinary skill in the art in view of the teachings herein. For example, the anvil may be introduced into or retracted from a naturally occurring body lumen of tissue (2), which may be the intestine, esophagus (4), or some other portion of the gastrointestinal (GI) tract.

With respect to a trans-oral introduction of the anvil, the anvil may be introduced trans-orally and directed downward into a patient's esophagus (4) to a first suturing position shown in, for example, FIG. 2A (wherein tissue (2) may represent the esophagus). The anvil may then be sutured in the first suturing position as shown in FIG. 2A and as described above with respect to anvil (40). The anvil may additionally or alternatively be attached to tissue (2), as shown in FIG. 2A in any suitable manner as will be apparent to those of ordinary skill in the art in view of the teachings herein. Stapling head assembly (20) may be introduced via, for example, an abdominal opening and led up esophagus (4) to a second suturing position disposed below the first suturing position. Stapling head assembly (20) may then be sutured to tissue (2) as described above or attached in any suitable manner as will be apparent to those of ordinary skill in the art in view of the teachings herein. Anvil (40) and stapling head assembly (20) are then operable to interact to sever and staple tissue (2) as described above to create anastomosis (6) (created by two reconnected portions of tissue (2)) as shown in FIGS. 7A-9, which are described in greater detail further below.

Additional exemplary modifications that may be provided for instrument (10) to reduce esophageal trauma during transport of anvil (40) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

A. Exemplary First Tilting Anvil Version Including Multiple Pivots

Figure 7A:
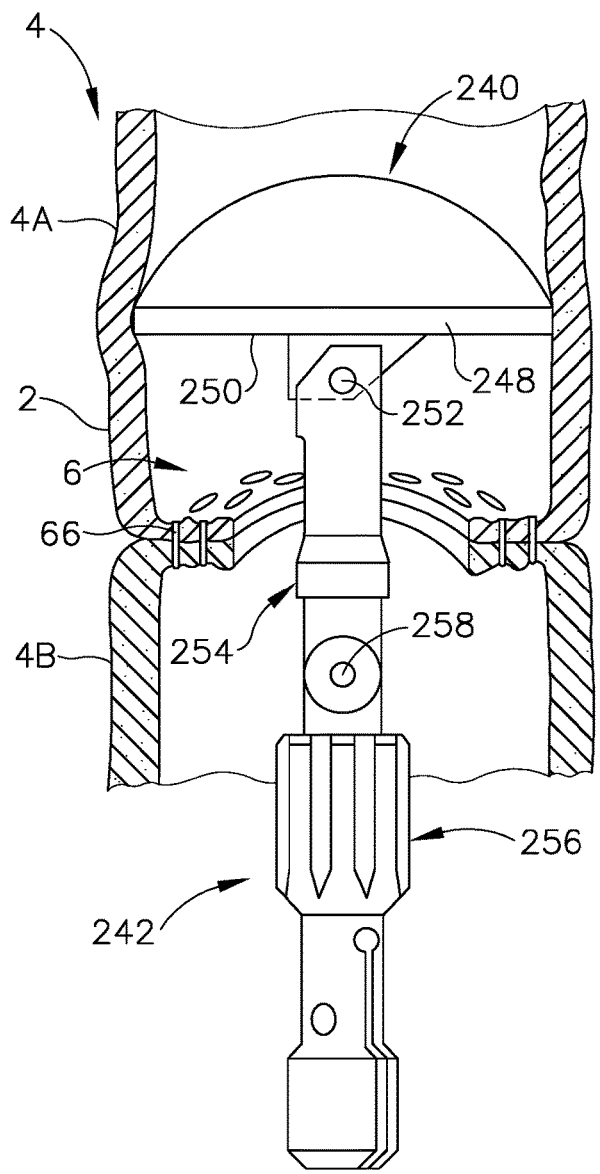
FIG. 7A depicts a partial, cross-sectional perspective view of an exemplary anvil in a first position in which the anvil has interacted with a stapling head assembly to create an anastomosis.
Figure 7B:
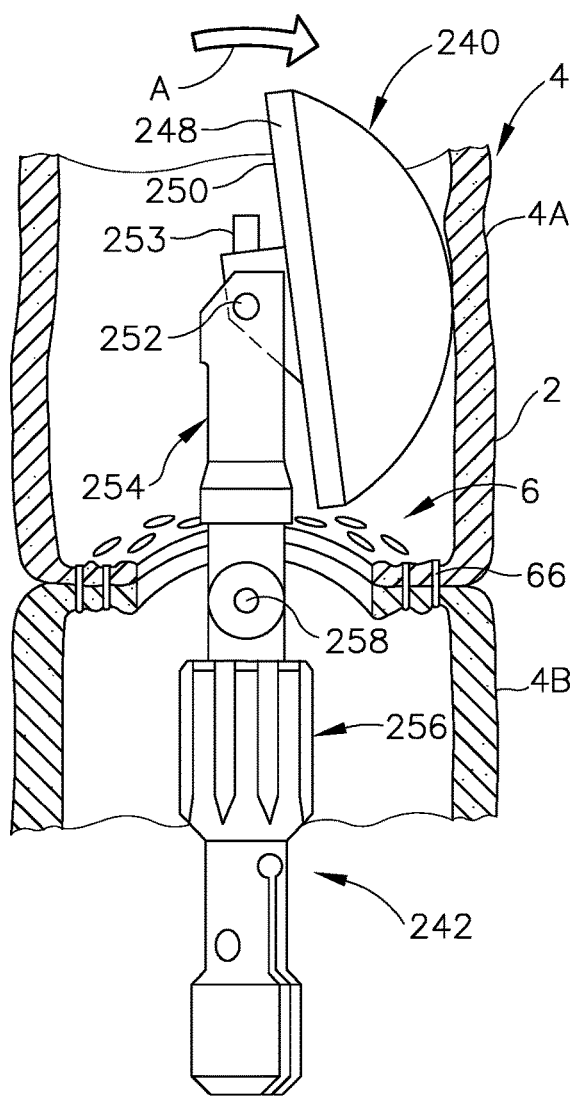
FIG. 7B depicts a partial, cross-sectional perspective view of the anvil of FIG. 7A in a second position in which an anvil head of the anvil has been tilted away from a link and an anvil shaft portion.
Figure 7C:
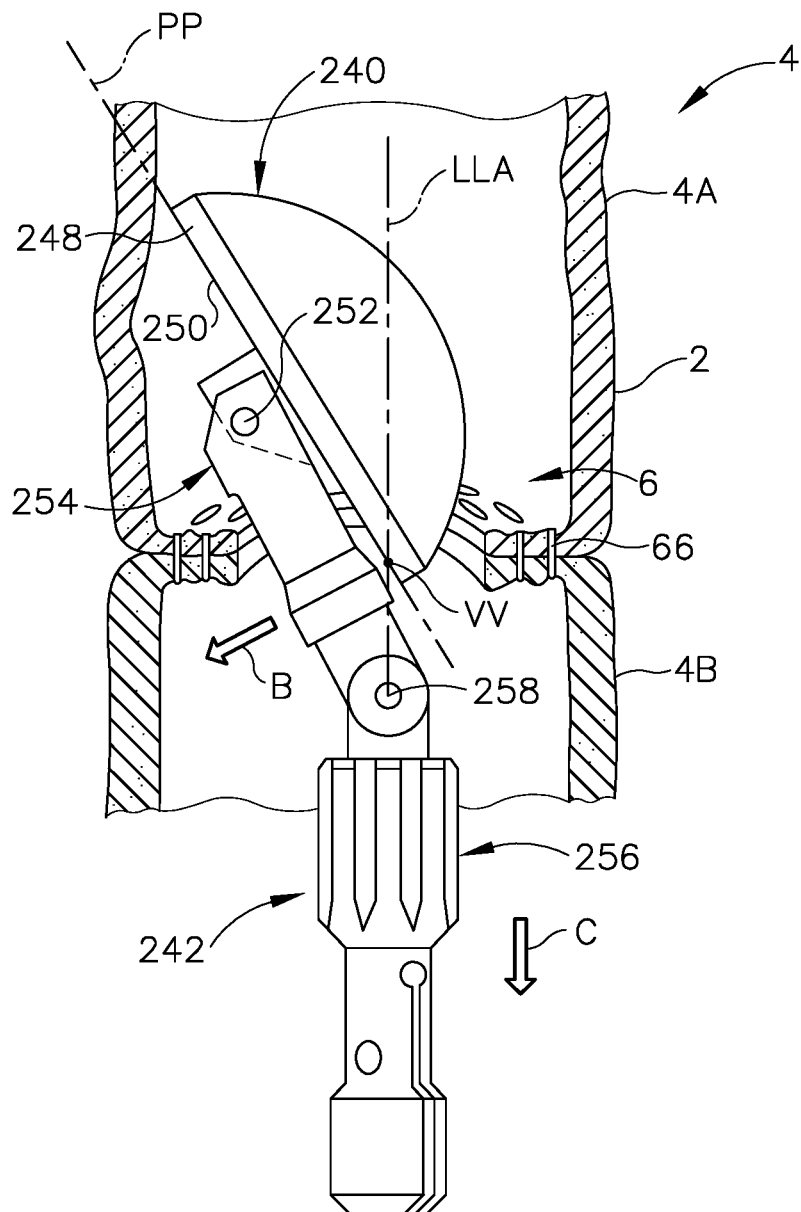
FIG. 7C depicts a partial, cross-sectional perspective view of the anvil of FIG. 7A in a third position in which a link of the anvil shaft is tilted away from the anvil shaft portion.

As shown in FIGS. 7A-7C, an exemplary first tilting anvil (240) includes anvil head (248) and a proximal shaft (242) extending proximally from anvil head (248). Proximal shaft (242) is attachable to trocar (38) in a manner as described above with respect to proximal shaft (42) or as will be apparent to one of ordinary skill in the art in view of the teachings herein. Proximal shaft (242) comprises a flexible material, a rigid material, or any suitable material as will be apparent to one of ordinary skill in the art in view of the teachings herein. Anvil head (248) is similar to anvil head (48), described above, and includes a plurality of staple forming pockets (not shown) formed in a proximal face (250) of anvil head (248). Anvil head (248) operates with staples (66) in a similar manner as described above for anvil head (48).

Anvil head (248) is linked to proximal shaft (242). Proximal shaft (242) includes link (254) and shaft portion (256). Link (254) and shaft portion (256) are linked together via linking pivot (258). Link (254) is rotatable about a longitudinal axis of linking pivot (258). Anvil head (248) is linked to link (254) via head pivot (252). Anvil head (248) is rotatable about a longitudinal axis of head pivot (252) in the direction of arrow (A), as shown in FIG. 7B. Link (254) of proximal shaft (242) is rotatable about linking pivot (258) in the direction of arrow (B), as shown in FIG. 7C. Head pivot (252), and other pivots of the present disclosure, may be comprised of, for example, pins received through channels or other suitable structures as will be apparent to those of ordinary skill in the art in view of the teachings herein.

As shown in FIG. 7B, driver rod (253) is disposed and translatable within proximal shaft (242). When driver rod (253) is advanced to a distal position, driver rod (253) engages an off-center point of proximal face (250) of anvil (240) with sufficient force to tilt anvil head (248) about head pivot (252) in the direction of arrow (A). Driver rod (253) keeps anvil head (248) in the tilted position while driver rod (253) is in the distal position. In some versions, driver rod (253) is retracted proximally before link (254) rotates about linking pivot (258) as shown in FIG. 7C. In some other versions, driver rod (253) stays in the distal position when link (254) rotates about linking pivot (258). It should therefore be understood that driver rod (253) may either proximally terminate distal to linking pivot (258); or driver rod may flex through linking pivot (258).

In some versions, the longitudinal position of driver rod (253) relative to anvil head (248) is based on the position of anvil (240) in relation to stapling head assembly (20). For instance, driver rod (253) may be configured to remain in the distal position whenever anvil (240) is decoupled from trocar (38) of stapling head assembly (20). In some such versions, driver rod (253) may automatically retract proximally upon coupling anvil (240) with trocar (38). Alternatively, driver rod (253) may be configured to remain in the distal position even after anvil (240) is coupled with trocar (38), when anvil (240) is still spaced significantly from stapling head assembly (20) (e.g., before anvil (240) is drawn toward stapling head assembly (20) by trocar (38) to clamp tissue between anvil (240) and stapling head assembly (20), etc.). In some such versions, a feature in anvil (240) and/or a feature in stapling head assembly (20) may be configured to retract driver rod (253) proximally, thereby allowing anvil head (248) to pivot to the position shown in FIG. 7A, when anvil (240) is retracted within a certain distance relative to stapling head assembly (20). For instance, a camming feature of proximal shaft (242) may interact with a complementary feature of stapling head assembly (20) when proximal shaft (242) is retracted to a certain position within stapling head assembly (20). Instead of automating the retraction of driver rod (253), a separate actuator may extend along shaft assembly (60) to actuator handle assembly (70), enabling the operator to selectively advance/retract driver rod (253) independently. As still another variation, driver rod (253) may be integral with shaft portion (256), and the combination of driver rod (253) and shaft portion (256) may selectively slide relative to link (254) and pivot (258) to selectively advance/retract driver rod (253). As yet another merely illustrative example, an electromechanical feature (e.g., solenoid, etc.) may be used to selectively advance/retract driver rod (253) in an automated fashion or in a manual/independent fashion. Other suitable ways in which driver rod (253) may be actuated will be apparent to those of ordinary skill in the art in view of the teachings herein.

In use, anvil (240) is inserted into an interior lumen of tissue (2) in an anvil inserting direction. For instance, anvil (240) may be inserted trans-orally into esophagus (4) of a patient. Before anvil (240) is inserted, a portion of esophagus (4) may be resected and removed (e.g., using an endocutter type of linear cutting/stapling device), resulting in separation of upper esophagus (4A) from lower esophagus (4B). Anvil (240) may be fed down upper esophagus (4A) until it reaches the bottom end of upper esophagus (4A), where instrument (10) may be used to join upper esophagus (4A) and lower esophagus (4B) through an end-to-end anastomosis (6). Anvil (240) may be in positions shown in FIG. 7B or 7C while being inserted, for example, and prior to shaft portion (256) being secured to a trocar of a stapling head assembly, such as in the manner described above to attach anvil (40) to trocar (38) and stapling head assembly (20). In some versions, conventional surgical graspers are inserted through esophagus (4) to grasp shaft portion (256) and thereby pull anvil (240) to the anastomosis site via upper esophagus (4A).

Anvil (240) may be straightened into a position as shown in FIG. 7A prior to interacting with stapling head assembly (20) as described above. Stapling head assembly (20) is advanced toward anvil (240) through lower esophagus (4B) in a stapling direction that is opposite the anvil inserting direction. Shaft portion (256) is then coupled with trocar (38). The force deployed by the firing and stapling system as described above may straighten anvil (240) and shaft portion (256) into the position shown in FIG. 7A (for example, when instrument (10) clamps tissue between stapling head assembly (20) and anvil head (248)). The positions will be described further below with respect to a retraction of anvil (240). Anvil (240) may then be used as described above to staple tissue (2) with staples (66). FIG. 7A shows a position after which anvil (240) has been used to staple tissue (2) with staples (66), and after which knife (36) has severed tissue, thereby creating a secure anastomosis (6).

To retract anvil (240), driver rod (253) is distally advanced, causing anvil head (248) to pivot about head pivot (252) in the direction of arrow (A) shown in FIG. 7B. Remaining in an extended position, driver rod (253) assists to maintain anvil head (248) in the first flipped or tilted position shown in FIG. 7B in a manner as will be apparent to those of ordinary skill in the art in view of the teachings herein. For example, driver rod (253) may contain a laterally offset portion (not shown) that abuts against proximal face (250) when driver rod (253) is in the extended position. The laterally offset portion thus prevents anvil head (248) from rotating back to the position of anvil head (248) shown in FIG. 7A.

Shaft portion (256) is proximally retracted along the direction of arrow (C) to retract anvil (240) through the lumen defined by tissue (2) (such as the esophagus (4)). Load on anvil head (248) from this retraction may provide the pivoting at linking pivot (258). For example, anvil head (248) may abut inner surface walls of tissue (2), causing link (254) to pivot about linking pivot (258) at angles of from about 30 degrees to about 45 degrees with respect to shaft portion (256) as anvil (240) is retracted proximally. Further, anvil head (248) is pivoted about head pivot (252) such that anvil head (248) may be retracted within an internal passageway of tissue (2) with minimal interaction with the inner surface walls of tissue (2). In other words, the above-described tilting and pivoting may prevent the outer edge of anvil head (248) from scraping against the inner wall of esophagus (4) as anvil (240) is transported through esophagus. In the position shown in FIG. 7C, for example, link (254) is tilted with respect to shaft portion (256) and anvil head (248) is tilted with respect to link (254) into a retraction position.

A plane of anvil head (248) depicted as plane (PP) in FIG. 7C defines an acute angle with longitudinal axis (LLA) of shaft portion (256) of proximal shaft (242), with vertex (VV) of the angle being positioned proximal in relation to head pivot (252). In the retraction position, a retraction of anvil (240) in the direction of arrow (C) substantially avoids snagging a most proximal portion of anvil head (248), disposed closest to linking pivot (258), with an interior surface of tissue (2), and particularly with edges of anastomosis (6) that are shown as stapled together via staples (66).

Driver rod (253) may remain extended during retraction of anvil (240) as described above. Further, anvil head (248) may be lockable at either the position shown in FIG. 7B or the position shown in FIG. 7C to ease extraction of anvil head (248) from anastomosis (6) to reduce anastomosis trauma during the retraction of anvil (240). For example, an internal projection in link (254) may be received in an internal notch in shaft portion (256) laterally offset from linking pivot (258) and disposed at a location to lock link (254) at a desired tilting angle with respect to shaft portion (256). By way of example only, shaft portion (256) may selectively slide relative to link (254) and pivot (258) to selectively lock the tilted angle of link (254) at pivot (258).

In some versions, anvil head (248) is resiliently biased to tilt to the position shown in FIGS. 7B and 7C. In such versions, driver rod (253) may be omitted (or still be included). In addition or in the alternative, link (254) may be resiliently biased to tilt to the position shown in FIG. 7C. Various suitable ways in which such biases may be provided will be apparent to those of ordinary skill in the art in view of the teachings herein. It should also be understood that, in such versions, link (254) and anvil head (248) may eventually tilt to the positions shown in FIG. 7A once anvil (240) is coupled with trocar (38) and anvil (240) is retracted toward stapling head assembly (20). In other words, the internal axial passageway within stapling head assembly (20) may straighten link (254) and the distal face of stapling head assembly (20) may straighten anvil head (248).

Other suitable ways in which an anvil may include a multi-pivot shaft will be apparent to those of ordinary skill in the art in view of the teachings herein.

B. Exemplary Second Tilting Anvil Version Including Off-Center Pivot

Figure 8:
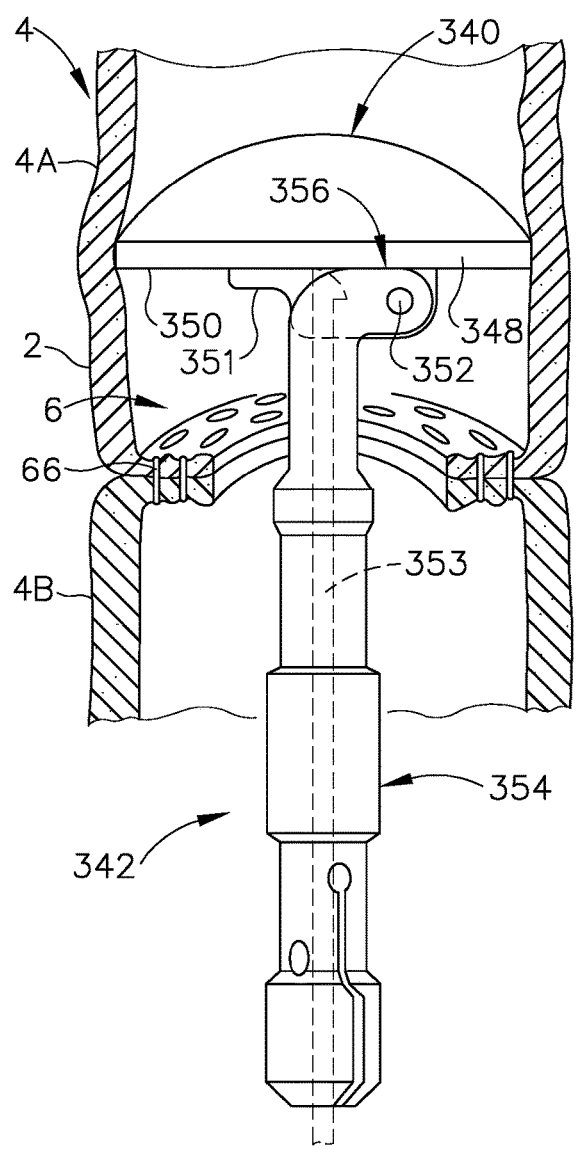
FIG. 8 depicts a partial cross-sectional, perspective view of another exemplary anvil in a first position in which the anvil has interacted with a stapling head assembly to create an anastomosis.
Figure 9:
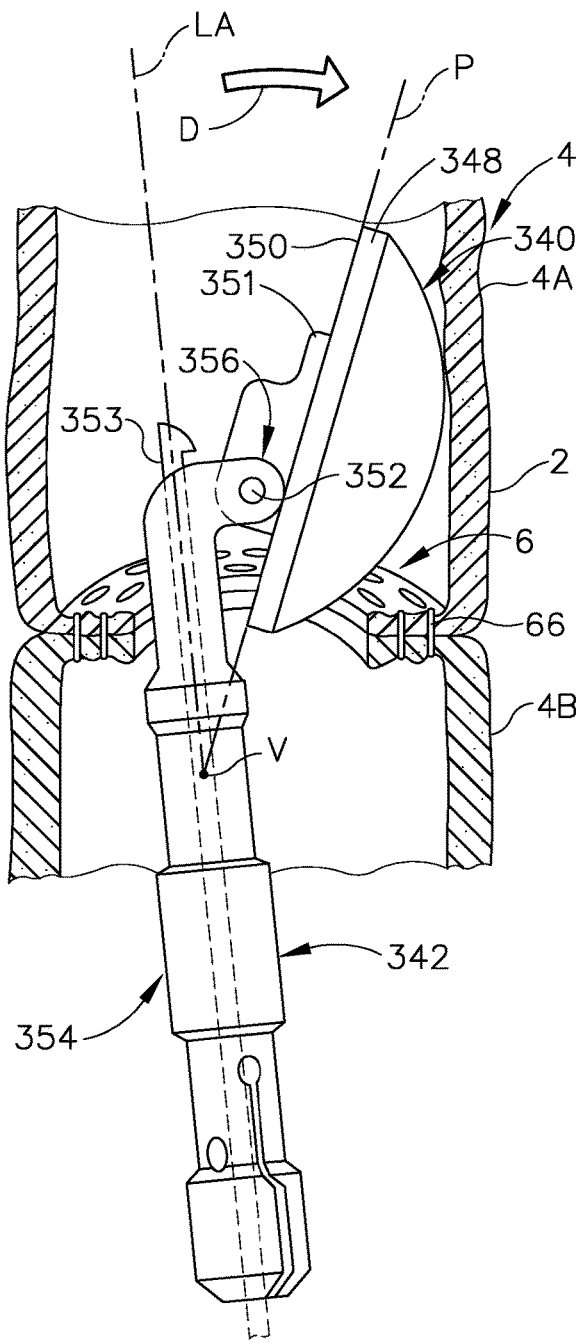
FIG. 9 depicts a partial cross-sectional, perspective view of the anvil of FIG. 8 in a second position in which an anvil head is tilted about an off-center pivot of an anvil shaft portion of the anvil.

FIGS. 8-9 show an exemplary second tilting anvil (340) including anvil head (348) and a proximal shaft (342) extending proximally from anvil head (348). Proximal shaft (342) is attachable to trocar (38) in a manner as described above with respect to proximal shaft (42) or as will be apparent to one of ordinary skill in the art in view of the teachings herein. Proximal shaft (342) comprises a flexible material, a rigid material, or any suitable material as will be apparent to one of ordinary skill in the art in view of the teachings herein. Anvil head (348) is similar to anvil head (48), described above, and includes a plurality of staple forming pockets (not shown) formed in a proximal face (350) of anvil head (348). Anvil head (348) operates with staples (66) in a similar manner as described above for anvil head (48).

Anvil head (348) includes linking connector (351), which connects anvil head (348) to proximal shaft (342). Anvil head (348) is linked to proximal shaft (342) via off-set head pivot (352). Anvil head (348) is rotatable about a longitudinal axis of head pivot (352) in the direction of arrow (D), as shown in FIG. 9. Driver rod (353) is disposed and translatable within proximal shaft (342) in a manner similar to that described for driver rod (253). Proximal shaft (342) includes a first portion (354) in which driver rod (353) is disposed and a second portion (356) extending laterally from a distal end of first portion (354) of proximal shaft (342). Head pivot (352) is disposed in second portion (356) and is off-set from the longitudinal axis of first portion (354). Head pivot (352) connects linking connector (351) of anvil head (348) to second portion (356) of proximal shaft (342), such that linking connector (351) and anvil head (348) are rotatable relative to second portion (356) about a longitudinal axis of head pivot (352).

In use, anvil (340) is inserted into an interior lumen of tissue (2) (e.g., upper esophagus (4A), etc.) in an anvil inserting direction in a manner similar to that described above for anvil (240). Anvil (340) may be in a position shown in FIG. 9 while being inserted, for example. When proximal shaft (342) is coupled with trocar (38), the clamping of tissue between stapling head assembly (20) and anvil (340) will straighten anvil (340) before a firing actuation as described above. Thus, the force deployed by the firing and stapling system as described above will straighten anvil (340) into the position shown in FIG. 8. Anvil (340) may then be used as described above to staple interior surfaces of tissue (2). FIG. 8 shows a position after which anvil (340) has been used to staple interior surfaces of a lumen of tissue (2) with staples (66) to create anastomosis (6).

To retract anvil (340), driver rod (353) is distally advanced, causing anvil head (348) to pivot about head pivot (352) in the direction of arrow (D) shown in FIG. 9. Driver rod (353) may remain advanced to assist in maintaining anvil head (248) in the tilted position shown in FIG. 9. Because second portion (356) is laterally off-set from first portion (354), anvil head (348) is able to rotate about head pivot (352) into a position in which anvil head (348) is at an obtuse angle with respect to a starting position of anvil head (348). In particular, anvil head (348) rotates more than 90 degrees with respect to proximal shaft (342) in the present example. A plane of anvil head (348) depicted as plane (P) in FIG. 9 defines an acute angle with longitudinal axis (LA) of proximal shaft (342), with the vertex (V) of the angle being at a position that is proximal in relation to head pivot (352). Thus, once flipped, a proximal end of anvil head (348) is disposed proximal in relation to second portion (356) and between ends of second portion (356) and first portion (354) of proximal shaft (342).

Anvil head (348) may be lockable at the obliquely angled position of FIG. 9 to ease extraction of anvil head (348) from anastomosis (6) in a manner similar to that described above to lock anvil head (248) as will be apparent to those of ordinary skill in the art in view of the teachings herein. For example, a projection on an interior surface of linking connector (351) may advance until receipt in a complementary notch disposed in an interior surface of second portion (356). Additionally or alternatively, a laterally projecting portion of drive rod (353) may be received into a notch disposed in an underside of linking connector (351). Other suitable ways in which drive rod (353) may be selectively locked in the distal position shown in FIG. 9 (or at least resiliently biased to the distal position shown in FIG. 9) will be apparent to those of ordinary skill in the art in view of the teachings herein.

First portion (354) is proximally retracted downwardly through esophagus (4) to retract anvil (340) from esophagus (4) in a manner as described above. Load on anvil head (348) from this retraction may cause proximal shaft (342) to tilt in a direction opposite arrow (D) while within esophagus (4), such that longitudinal axis (LA) of proximal shaft (342) is tilted relative to the axis of esophagus (4). With anvil head (348) and proximal shaft (342) tilted (as shown in FIG. 9), anvil head (348) may be retracted downwardly esophagus (4) with minimal interaction between the outer edge of anvil head (348) and the inner surface walls of esophagus (4). In other words, the above-described tilting and pivoting may prevent the outer edge of anvil head (348) from scraping against the inner wall of esophagus as anvil (340) is transported through esophagus.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of using a surgical instrument, the surgical instrument comprising: (a) a stapling head assembly; and (b) an anvil including (i) an anvil head having a proximal face, (ii) a shaft including a distal shaft portion and a proximal shaft portion that defines a central axis of the anvil, (iii) a first pivot defining a first pivot axis, (iv) a second pivot spaced proximally from the first pivot and defining a second pivot axis, and (v) a driver rod movably disposed within the shaft, the method comprising:
   (a) inserting the anvil into an anatomical passageway; and
   (b) actuating the driver rod to engage the anvil head and thereby pivoting the anvil head about the first pivot axis from a first position to a second position while the first pivot axis remains stationary relative to the central axis, wherein in the first position the proximal face of the anvil is transversely positioned relative to the central axis and in the second position the proximal face of the anvil is obliquely angled relative to the central axis.

2. The method of claim 1, wherein the step of actuating the driver rod to engage the anvil head and thereby pivot the anvil head about the first pivot axis from the first position to the second position occurs after the step of inserting the anvil into the anatomical passageway.

3. The method of claim 1, further comprising removing the anvil from the anatomical passageway.

4. The method of claim 3, wherein the second pivot axis intersects the central axis, further comprising pivoting the anvil head about the second pivot axis.

5. The method of claim 4, wherein the anvil head is configured to pivot about the first pivot axis relative to the distal shaft portion in a first pivoting direction, and the distal shaft portion is configured to pivot about the second pivot axis relative to the proximal shaft portion in a second pivoting direction, wherein the first pivoting direction is opposite the first pivoting direction.

6. The method of claim 5, wherein the step of removing the anvil head creates engagement between the anvil head and an inner surface of the anatomical passageway, wherein the engagement of the anvil head and the inner surface of the anatomical passageway pivots the distal shaft portion about the second pivot axis.

7. The method of claim 1, wherein the anatomical passageway comprises a first passageway and a second passageway, wherein the step of inserting the anvil into the anatomical passageway includes inserting the anvil into one of the first passageway or the second passageway and inserting the stapling head assembly into the other of the first passageway or the second passageway.

8. The method of claim 7, further comprising coupling the stapling head assembly with the anvil.

9. The method of claim 8, further comprising compressing tissue of the first passageway and the second passageway between the stapling head assembly and the anvil.

10. The method of claim 9, further comprising driving staples through the first and second passageways thereby joining the first and second passageways.

11. The method of claim 7, wherein the anatomical passageway includes an esophagus, wherein the first passageway is an upper esophagus and the second passageway is a lower esophagus.

12. The method of claim 11, wherein the second pivot axis pivots the distal shaft portion relative to the proximal shaft portion at angles from about 30 degrees to about 45 degrees.

13. The method of claim 1, wherein the step of actuating the driver rod to engage the anvil head further includes translating the driver rod in a direction parallel to the central axis from a retracted position to an extended position, wherein the driver rod in the retracted position permits the anvil head to remain in the first position and the driver rod in the extended position urges the anvil head toward the second position.

14. The method of claim 13, further comprising maintaining the driver rod in the extended position and thereby preventing the anvil from returning to the first position.

15. A method of using a surgical instrument, the surgical instrument comprising: (a) a stapling head assembly; and (b) an anvil including: (i) an anvil head having a proximal face, (ii) a shaft defining a central axis, wherein the shaft includes a distal shaft portion and a proximal shaft portion, (iii) a first pivot defining a first pivot axis and coupling the anvil head to the distal shaft portion, (iv) a second pivot defining a second pivot axis and coupling the distal shaft portion to the proximal shaft portion, and (v) a driver rod movably disposed within the shaft, the method comprising:
   (a) moving the driver rod from a proximal position to a distal position in which a distal end of the driver rod extends distally beyond a distal-most end of the shaft to thereby urge the anvil head to pivot about the first pivot axis from a perpendicular position towards a non-perpendicular position, wherein in the perpendicular position the proximal face of the anvil head is perpendicular relative to the central axis and in the non-perpendicular position the anvil head is non-perpendicular relative to the central axis; and
   (b) inserting the anvil within a severed anatomical passageway.

16. The method of claim 15, further comprising maintaining the driver rod in the distal position to thereby prevent the anvil head from pivoting from the non-perpendicular position to the perpendicular position.

17. The method of claim 16, further comprising retracting the anvil proximally through the anatomical passageway and thereby creating contact between the anvil head and an inner wall of the anatomical passageway.

18. The method of claim 17, wherein the step of creating contact between the anvil head and the inner wall of the anatomical passageway pivots the proximal shaft portion about the second pivot.

19. A method of using a surgical instrument, the surgical instrument comprising: (a) a stapling head assembly; (b) an anvil including: (i) an anvil head having a proximal face, (ii) a first shaft portion extending proximally from the anvil head, (iii) a first pivot defining a first pivot axis rotatably coupling the first shaft portion to the anvil head, (iv) a second shaft portion, and (v) a second pivot defining a second pivot axis rotatably coupling the first shaft portion to the second shaft portion, the method comprising:
- (a) inserting the anvil within an esophagus of a patient;
- (b) pivoting the anvil head relative to the first shaft portion about the first pivot axis in a first rotational direction; and
- (c) pivoting the first shaft portion relative to the second shaft portion about the second pivot axis in a second rotational direction and thereby advancing the first pivot axis in the second rotational direction while the anvil head remains stationary relative to the first shaft portion, wherein the second rotational direction is opposite the first rotational direction.

20. The method of claim 19, wherein the step of pivoting the first shaft portion relative the second shaft portion about the second pivot axis further includes pivoting the first shaft portion by about 30 degrees to about 45 degrees relative to the second shaft portion.

* * * * *